United States Patent [19]

Schein et al.

[11] Patent Number: 5,292,497

[45] Date of Patent: Mar. 8, 1994

[54] METHOD OF REDUCING CHEMOTHERAPY TOXICITY USING (METHYLAMINOPROPYLAMINO)PROPYL DIHYDROGEN PHOSPHOROTHIOATE

[75] Inventors: Philip S. Schein, Bryn Mawr, Pa.; James R. Piper, Birmingham, Ala.

[73] Assignee: U.S. Bioscience, Inc., West Conshohocken, Pa.

[21] Appl. No.: 39,690

[22] Filed: Mar. 29, 1993

Related U.S. Application Data

[63] Continuation of Ser. No. 918,784, Jul. 27, 1992, abandoned, which is a continuation of Ser. No. 798,046, Nov. 27, 1991, abandoned, which is a continuation of Ser. No. 532,245, Jun. 5, 1990, abandoned, which is a continuation of Ser. No. 136,721, Dec. 22, 1987, abandoned.

[51] Int. Cl.$^5$ .................. A61K 49/00; A61K 31/54; A61K 31/44; A61K 31/685
[52] U.S. Cl. ..................... 424/10; 514/269; 514/299; 514/917; 514/76; 514/546; 514/663
[58] Field of Search .............. 424/10; 514/299, 269, 514/917, 76, 546, 663

[56] References Cited

U.S. PATENT DOCUMENTS

| | | | |
|---|---|---|---|
| 3,629,410 | 12/1971 | Heiffer et al. | 424/211 |
| 3,892,824 | 7/1975 | Piper | 424/211 |
| 4,314,989 | 2/1982 | Rosen | 424/10 |
| 4,356,306 | 10/1982 | Bär et al. | 424/258 |
| 4,424,216 | 1/1984 | Cerami et al. | 424/211 |
| 4,510,147 | 4/1985 | Bär et al. | 514/314 |
| 4,656,034 | 4/1987 | Sarnoff | 424/94 |
| 4,657,928 | 4/1987 | Sorenson | 514/499 |
| 4,676,979 | 6/1987 | Schellenberg et al. | 424/80 |

OTHER PUBLICATIONS

Furukawa et al., Chem. Abst. 106(9):61084j (1987).
N. F. Tabachnik et al, "Studies on the Reduction of Sputum Viscosity in Cystic Fibrosis Using an Orally Absorbed Protected Thiol," *J. Pharmacol. Exp. Ther.*, vol. 214, No. 2, pp. 246-249, 1980.
F. Valeriote, Ph.D. et al., "Dose and Inteval Relationship for the Interaction of WR-2721 . . .", *International Journal Radiation, Oncology, Biol. Phys.*, vol. 10, pp. 1561-1564.
F. Valeriote et al., "Protection and Potentiation of Nitrogen Mustard Cytotoxicity by WR-2721", *Cancer Research*, vol. 42, pp. 4330-4331, 1982.
T. H. Wasserman, M. D. et al., "Differential Protection Against Cytotoxic Chemotherapeutic Effects on Bone Marrow CFUs by WR-2721," *Cancer Clinical Trials*, vol. 4, pp. 3-6, 1981.
J. M. Yuhas, "Active Versus Passive Absorption Kinetics as the Basis for Selective Protection . . . ," *Cancer Research*, vol. 40, pp. 1519-1524, 1980.
T. R. Sweeney, "A Survey of Compounds from the Antiradiation Drug Development Program . . . ," Walter Reed Army Institute of Research, Sep. 1979.

*Primary Examiner*—Frederick E. Waddell
*Assistant Examiner*—Gregory Hook
*Attorney, Agent, or Firm*—Wegner, Cantor, Mueller & Player

[57] ABSTRACT

A method of decreasing the toxicity of chemical therapeutic agents administered in cancer chemotherapy including adminstration to a patient undergoing chemotherapy. This reduction in toxicity can be accomplished by administering an effective amount of S-3-(3-methylaminopropylamino)propyl dihydrogen phosphorothioate. Methods of inducing mucolytic activity and reducing toxicity of acetominophen overdose are also discussed. Such activities are induced through the administration of S-3-(3-methylaminopropylamino)propyl dihydrogen phosphorothioate.

4 Claims, No Drawings

METHOD OF REDUCING CHEMOTHERAPY TOXICITY USING (METHYLAMINOPROPYLAMINO)PROPYL DIHYDROGEN PHOSPHOROTHIOATE

This application is a continuation of U.S. application Ser. No. 07/918,784 filed Jul. 27, 1992 now abandoned which is a continuation of Ser. No. 07/798,046 filed Nov. 27, 1991; now abandoned which is a continuation of Ser. No. 07/532,245 filed Jun. 5, 1990; now abandoned which is a continuation of ser. No. 07/136,721 filed Dec. 22, 1987, now abandoned.

BACKGROUND OF THE INVENTION

Cancer chemotherapy has been practiced for many years with many different therapeutic agents. A major drawback of this therapy scheme is the toxicity of the chemotherapeutic agents. Agents capable of destroying invading cancer cells are unfortunately often quite toxic to normal cells. Thus, employers of and recipients of chemotherapeutic techniques have a great need for either non-toxic (to normal cells) therapeutic agents or additional agents capable of decreasing the toxicity of chemotherapeutic agents. The present invention is directed toward an agent for decreasing the toxicity of a wide spectrum of chemotherapeutic agents.

Dihydrogen phosphorothioate compounds are known to be effective as antiradiation agents. See U.S. Pat. No. 3,892,824 to Piper et al and Sweeney, *A Survey of Compounds from the Antiradiation Drug Development Program of the U.S. Army Medical Research and Development Command*, published by the Walter Reed Army Institute of Research, Washington D.C. (1979).

Also, many disease conditions such as cystic fibrosis involve an increase in the viscosity of sputum in a patient suffering therefrom. Thus, methods of decreasing that viscosity are in demand.

SUMMARY OF THE INVENTION

The present invention involves a method for decreasing the toxicity of chemotherapeutic agents and a method for inducing mucolytic activity through the oral administration of S-3-(3-methylaminopropylamino)propyl dihydrogen phosphorothioate. Since these chemical therapeutic agents are often administered frequently in a treatment regimen, methods for decreasing the toxicity of the same are in demand.

DETAILED DESCRIPTION OF THE INVENTION

The first aspect of the present invention is directed toward a method of decreasing the toxicity of chemical therapeutic agents administered in cancer chemotherapy comprising oral or intravenous adminstration to a patient undergoing said chemotherapy of an effective amount of S-3-(3-methylaminopropylamino)propyl dihydrogen phosphorothioate.

The second aspect of the present invention provides a method of inducing mucolytic activity to decrease the viscosity of sputum comprising oral, intravenous or inhalation adminstration to a patient in need of such a viscosity reduction of an effective amount of S-3-(3-methylaminopropylamino)propyl dihydrogen phosphorothioate.

The third aspect of the present invention provides a method of reducing hepato toxicity of acetominaphen overdosage through the oral or intravenous adminstration to a patient in need of such a reduction of an effective amount of S-3-(3-methylaminopropylamino)propyl dihydrogen phosphorothioate.

S-3- (3-methylaminopropylamino)propyl dihydrogen phosphorothioate can be depicted as follows:

S-3-(3-methylaminopropylamino)propyl dihydrogen phosphorothioate may be prepared in accordance with the procedure described in U.S. Pat. No. 3,892,824.

By chemical therapeutic agents, there is contemplated the chemicals or compositions administered to cancer patients during the course of the patient's chemotherapy Exemplary of such chemotherapeutic agents are alkylating agents such as cyclophosphamide, melphalan and nitrogen mustard, as well as platinum agents such as carboplatin and cisplatin.

By mucolytic activity there is contemplated the reduction in viscosity of sputum. Such activity is important in the treatment of disease conditions that exhibit the symptom of increased viscosity of sputum. Exemplary of such conditions is cystic fibrosis.

The reduction in hepato toxicity of acetominaphen overdosage is accomplished by providing "reducing equivalents" (i.e. an external source of sulfhydryl groups). This can be accomplished through the administration of S-3-(3-methylaminopropylamino)propyl dihydrogen phosphorothioate.

By oral administration, there is contemplated the preparation of S-3-(3-methylaminopropylamino)propyl dihydrogen phosphorothioate in any dosage form capable of oral administration. Such dosage forms include tablets, capsules, caplets, solutions and the like.

The oral dosage forms of the present invention may contain pharmaceutically acceptable inert ingredients. As such inert ingredients there are contemplated pharmaceuticals, carriers, excipients, fillers, etc. which do not interfere with the activity of the compound.

Also, fillers such as clays or siliceous earth may be utilized if desired to adjust the size of the dosage form.

Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

Also in accordance with the present invention, there is provided a liquid-based dosage form suitable for the administration of the composition to a patient. The liquid base for this dosage form may be any liquid capable of transporting the composition into the body of a patient without disrupting the activity of the compound or harm the patient. Exemplary of such a liquid is an isotonic solution. The isotonic solution may also contain conventional additives therein such as sugars. These solutions can be used in the preparation of oral, intravenous or inhalation composition.

Thus, the compositions of the present invention may be admixed according to known procedures using known excipients.

As an effective amount of the compound of the first aspect of the present invention, there is contemplated any amount which would serve to decrease the toxicity of chemotherapeutic agents. For example, a dosage of between about 50 to about 2500 mg/m$^2$ body surface area of the patient is contemplated. A preferred dosage according to the present invention is from about 300 to about 1000 mg/m$^2$ body surface area of the patient. The active ingredient may be administered in single or divided doses.

As an effective amount of the compound of the second aspect of the present invention, there is contemplated any amount which would serve to induce mucolytic activity in a patient in need thereof. For example, a dosage of between about 50 to about 2500 mg/m$^2$ body surface area of the patient is contemplated. A preferred dosage according to the present invention is from about 300 to about 1000 mg/m$^2$ body surface area of the patient. The active ingredient may be administered in single or divided doses.

As an effective amount of the compound of the third aspect of the present invention, there is contemplated any amount which would serve to reduce the toxicity of acetaminophen overdose. For example, a dosage of between about 50 to about 2500 mg/m$^2$ body surface area of the patient is contemplated. A preferred dosage according to the present invention is from about 300 to about 1000 mg/m$^2$ body surface area of the patient. The active ingredient may be administered in single or divided doses.

Illustrative examples of the present invention follow.

EXAMPLE I 1000 mg of S-3-(3-methylaminopropylamino)propyl dihydrogen phosphorothioate is suspended in an isotonic solution. 200 mg/m$^2$ body surface area of S-3-(3-methylaminopropylamino)propyl dihydrogen phosphorothioate thus suspended is administered to a patient undergoing chemotherapy with cisplatin.

EXAMPLE II 500 mg of S-3-(3-methylaminopropylamino)propyl dihydrogen phosphorothioate is suspended in an isotonic solution. 500 mg/m$^2$ body surface area of S-3-(3-methylaminopropylamino)propyl dihydrogen phosphorothioate thus suspended is administered to a patient undergoing chemotherapy with nitrogen mustard.

EXAMPLE III 1000 mg of S-3-(3-methylaminopropylamino)propyl dihydrogen phosphorothioate is admixed with hydroxypropylcellulose and stearyl alcohol. The mixture is then compressed into tablet form. 200 mg/m: body surface area of S-3-(3-methylaminopropylamino)propyl dihydrogen phosphorothioate thus prepared is administered to a patient undergoing chemotherapy with cyclophosphamide, N,N-bis(2-chloroethyl)tetrahydro-2H-1,3,2-oxazaphosphorin-2-amine.

EXAMPLE IV 700 mg of S-3-(3-methylaminopropylamino)propyl dihydrogen phosphorothioate is admixed with hydroxypropylcellulose and glycowax. The mixture is then compressed into tablet form. 500 mg/m$^2$ body surface area of S-3-(3-methylaminopropylamino)propyl dihydrogen phosphorothioate thus prepared is administered to a patient undergoing chemotherapy with melphalan, 4-[bis(2-chloroethyl)amino]-L-phenylalanine.

EXAMPLE V 1000 mg of S-3-(3-methylaminopropylamino)propyl dihydrogen phosphorothioate is suspended in an isotonic solution. 200 mg/m$^2$ body surface area of S-3-(3-methylaminopropylamino)propyl dihydrogen phosphorothioate thus suspended is administered to a patient suffering from cystic fibrosis.

EXAMPLE VI 1000 mg of S-3-(3-methylaminopropylamino)propyl dihydrogen phosphorothioate is admixed with hydroxypropylcellulose and stearyl alcohol. The mixture is then compressed into tablet form. 200 mg/m$^2$ body surface area of S-3-(3-methylaminopropylamino)propyl dihydrogen phosphorothioate thus prepared is administered to a patient suffering from cystic fibrosis.

EXAMPLE VII 1000 mg of S-3-(3-methylaminopropylamino)propyl dihydrogen phosphorothioate is suspended in an isotonic solution. 200 mg/m$^2$ body surface area of S-3-(3-methylaminopropylamino)propyl dihydrogen phosphorothioate thus suspended is administered to a patient suffering from acetaminophen overdose.

EXAMPLE VIII 1000 mg of S-3-(3-methylaminopropylamino)propyl dihydrogen phosphorothioate is admixed with hydroxypropylcellulose and stearyl alcohol. The mixture is then compressed into tablet form. 200 mg/m$^2$ body surface area of S-3-(3-methylaminopropylamino)propyl dihydrogen phosphorothioate thus prepared is administered to a patient suffering from acetaminophen overdose.

What is claimed is:

1. A method of decreasing the toxicity of alkylating agents and/or platinum anti-cancer agents administered in cancer chemotherapy comprising orally administering to a patient undergoing said chemotherapy an effective amount of S-3-(3-methylaminopropylamino)propyl dihydrogen phosphorothioate.

2. A method of claim 1, wherein said S-3-(3-methylaminopropylamino)propyl dihydrogen phosphorothioate is administered in an amount not greater than 2500 mg/m$^2$ body surface area of said patient.

3. A method of claim 1, wherein said S-3-(3-methylaminopropylamino)propyl dihydrogen phosphorothioate is administered in an amount of between about 300 and 1000 mg/m$^2$ body surface area of said patient.

4. A method of claim 1, wherein at least one member selected from the group consisting of cyclophosphamide, melphalan, nitrogen mustard, carboplatin and cisplatin is administered in the chemotherapy.

* * * * *